United States Patent [19]
McArthur

[11] Patent Number: 5,820,565
[45] Date of Patent: Oct. 13, 1998

[54] FLUSH VALVE WITH INTERLOCKING SEAL

[75] Inventor: Gregory R. McArthur, Sandy, Utah

[73] Assignee: Merit Medical System, Inc., South Jordan, Utah

[21] Appl. No.: 743,632

[22] Filed: Nov. 4, 1996

[51] Int. Cl.⁶ ...................................................... A62B 5/02
[52] U.S. Cl. ....................... 600/486; 600/561; 251/335.1; 604/256
[58] Field of Search ..................................... 600/485, 486, 600/488, 498, 500, 504, 505, 561; 604/30, 33, 34, 246–249, 256, 236; 251/335.1, 341, 342, 331–334; 137/510

[56] References Cited

U.S. PATENT DOCUMENTS

| | | | |
|---|---|---|---|
| 4,696,305 | 9/1987 | Von Berg | 600/486 |
| 4,934,375 | 6/1990 | Cole et al. | 600/486 |
| 4,936,542 | 6/1990 | Beard | 604/34 |
| 4,947,856 | 8/1990 | Beard | 600/486 |
| 5,048,537 | 9/1991 | Messinger | 600/486 |
| 5,171,230 | 12/1992 | Eland et al. | 604/246 |
| 5,269,311 | 12/1993 | Kirchner et al. | 600/435 |

*Primary Examiner*—Robert L. Nasser
*Assistant Examiner*—Bryan K. Yarnell
*Attorney, Agent, or Firm*—Workman Nydegger Seeley

[57] ABSTRACT

A flush valve comprising a fluid receiving housing having a first passageway, a fluid discharge housing having a second passageway, and a flow restricting means having a capillary tube defining a primary fluid flow path extending between the first passageway and the second passageway. An elastomeric sealing tube encircles and is biased against the exterior surface of the flow restricting means. A secondary fluid flow path extends from the first passageway to the second passageway between the interior surface of the sealing tube and the exterior surface of the flow restricting means so as to bypass the capillary tube. A connecting plate connects the fluid receiving housing to the fluid discharge housing. Projecting from the connecting plate, receiving housing, and discharge housing are individual pairs of clamping fingers that are longitudinally aligned to form a single U-shaped channel. The U-shaped channel is configured to selectively receive and retain an electrical cable from a blood pressure transducer when the flush valve is attached thereto. To selectively seal closed the secondary fluid flow passageway, an annular ridge projects from the interior surface of the sealing tube and interlocks with a complementary groove formed on the exterior surface of the flow restricting means.

44 Claims, 7 Drawing Sheets

FLUSH VALVE WITH INTERLOCKING SEAL

BACKGROUND OF THE INVENTION

1. The Field of the Invention

The present invention relates to flush valves and, more specifically, to flush valves attached to blood pressure transducers.

2. The Relevant Technology

Blood pressure transducers are used for invasive monitoring of heart rate and blood pressure of a patient. During conventional use, the blood pressure transducer is attached to a first or proximal end of a catheter tube while the opposing open distal end of the catheter tube is inserted within the body of a patient. The open distal end of the catheter tube is preferably positioned within a blood vessel (artery or vein) so as to be in communication with the circulatory system of the patient.

The catheter tube is filled with a saline solution which is in contact with the patient's blood at the distal end of the catheter tube. As the patient's heart pumps the blood, the pressure on the blood is transferred to the saline solution within the catheter tube. In turn, the pressure on the saline solution is transferred to the blood pressure transducer. The blood pressure transducer includes a diaphragm which flexes under the force of the saline solution. The frequency and force at which the diaphragm flexes is converted by the transducer to electrical signals. These signals are transferred to a monitor which displays the electrical signals as the heart rate and blood pressure of the patient.

One problem encountered with the above system is that blood diffusing within the saline solution at the distal end of the catheter tube can coagulate, forming blood clots within the catheter tube. The formation of blood clots not only effects the pressure readings on the blood pressure transducer but can also be dangerous to the patient. Should one of the blood clots dislodge from within the catheter tube and enter the blood stream, the blood clot could form a block within the circulatory system of a patient.

To help eliminate the formation of blood clots and to maintain the fluid level of the catheter tube, a fluid source, preferably a saline solution including an anti-blood coagulating agent, such as heparin, is attached to the blood pressure transducer up stream of the flexible diaphragm. Positioned between the blood pressure transducer and the fluid source, is an extremely small diameter capillary tube. The capillary tube minimizes the flow of the saline solution so that only the amount of saline solution necessary to prevent blood clotting and maintain the proper fluid level is allowed to flow through the blood pressure transducer and into the catheter tube. If the flow of the saline solution is too high, the saline solution can effect the reading of the blood pressure transducer. Furthermore, injecting too much solution within the blood stream can jeopardize the health of the patient.

The above disclosed fluid source is also typically used for initially filling the catheter tube with the saline solution prior to inserting the distal end of the catheter tube within the circulatory system of the patient. The catheter tube must be filled with the saline solution so as to remove all air from within the catheter tube. Any air bubbles remaining in the catheter tube can also affect the reading of the blood pressure transducer and can be lethal if introduced in the circulatory system of a patient. Because the capillary tube is so small, however, filling the catheter tube by fluid flowing through the capillary tube can take a prohibitively long time.

To remedy this problem, flush valves have been developed. A flush valve typically includes a rigid conduit having a smooth exterior surface with the capillary tube extending therethrough. The conduit is positioned within an elastomeric tube. The elastomeric tube has a smooth interior surface which compresses against the smooth exterior surface of the conduit. The conduit is configured, however, so that as the top to the elastomeric tube is pulled away from the exterior surface of the conduit, a secondary passageway is formed therebetween that bypasses the capillary tube. The secondary passageway allows for rapid filling of the catheter tube with the saline solution. When the elastomeric tube is released, the elastomeric tube constricts, sealing off the secondary passageway so that the saline solution must travel only through the capillary tube.

One of the problems frequently encountered with the prior art flush valves is their inability to maintain an effective seal of the secondary passageway. Once the elastomeric tube is released, it is often encountered that the interior surface of the elastomeric tube does not adequately seal against the exterior surface of the conduit. As a result, additional fluid continues to leak through the secondary passageway. This leaking is found to occur more frequently as the secondary passageway is increasingly opened and closed.

Leakage of fluids through the secondary passageway can be extremely dangerous to the patient. Excessive saline solution within the blood can cause excessive thinning of the blood, thereby affecting the blood pressure of the patient. Furthermore, the excess saline solution can over-saturate the patient, which can also have serious consequences. In addition, as the rate of leakage increases, the leaking can also affect the reading on the blood pressure transducer.

Another problem frequently encountered with the above discussed prior art blood monitoring systems is that a variety of cables, cords, and tubes are indiscriminately either attached to or project from the blood pressure transducer. The variety of cables and tubes can make it difficult to access and attach the flush valve. Furthermore, the various freely disposed cables and tubes can become easily entangled, resulting in confusion and disorganization of the patient treatment area, increasing patient care time and practitioner stress.

In addition, the electrical cable extending from the blood pressure transducer to the monitor is subject to bending and wear, particularly at the point where the cable is attached to the blood pressure transducer. The lack of support of the electrical cable at the attachment juncture may cause the cable to kink or fatigue at the juncture. As a result, the electrical cable may fail to properly transmit the signal from the transducer to the display monitor.

OBJECTS AND BRIEF SUMMARY OF THE INVENTION

It is therefore an object of the present invention to provide an improved flush valve for attachment to a blood pressure transducer.

Yet another object of the present invention is to provide flush valves as above that produce an increased effective seal to close off a secondary fluid flow path.

Another object of the present invention is to provide flush valves as above which minimize leaking of fluid through the secondary fluid flow path after repeated opening and closing of the secondary fluid flow path.

Yet another object of the present invention is to provide flush valves as above that minimize fatigue and kinking of the portion of the electrical cable projecting from the blood pressure transducer.

Another object of the present invention is to provide flush valves as above which help to organize and streamline cables and tubes attached to the blood pressure transducer.

Finally, another object of the present invention is to provide flush valves as above that are easily attached to the blood pressure transducer.

To achieve the forgoing objectives and in accordance with the invention as broadly disclosed and claimed herein, the present invention provides a flush valve including a fluid delivery means for dispensing fluid at a desired flow rate. In one embodiment, the fluid delivery means includes an inlet port, an outlet port, and a flow restricting means interposed between and coupled in fluid communication with the inlet port and outlet port. The flow restricting means has an exterior surface and a flow restricting passageway, the passageway defining a primary fluid flow path between the inlet port and the outlet port for dispensing a fluid at a desired flow rate. Typically, the flow restricting means comprises a capillary tube, the capillary tube defining the flow restricting passageway.

The flush valve further comprises sealing means for forming a seal about the exterior surface of the flow restricting means. The sealing means having an interior surface that is disposed about and biased against the exterior surface of the flow restricting means, the inlet port, and the outlet port. Thus, the fluid delivery means is received within the lumen of the sealing means so that the interior surface of the sealing means is biased against and forms a seal about the exterior surface of the fluid delivery means.

In addition, the flush valve includes bypass means for selectively forming a secondary fluid flow path between the inlet port and the outlet port, the secondary fluid flow path being formed between the exterior surface of the flow restricting means and the interior of the sealing means such that the secondary fluid flow path bypasses the primary fluid flow path.

To increase the seal between the sealing means and the flow restricting means, the exterior surface of the flow restricting means and the interior surface of the sealing means are configured so as to engage one another in an interlocking arrangement. In one embodiment, to effectively increase the seal between the sealing means and the flow restricting means, an annular ridge is formed encircling and radially projecting inwards from the interior surface of the sealing means. A groove complementary to the ridge is formed encircling the exterior surface of the flow restricting means. The ridge is received within the groove to form an interlocking engagement that seals closed the secondary fluid flow path. The ridge and groove configuration decreases the amount of force required by the sealing means to make an effective seal against the exterior surface of the fluid delivery means. As a result, a stronger seal is produced.

The flush valve further comprises securing means connected to the fluid delivery means and configured to engage a portion of the electrical cable of the transducer when the distal end of the fluid delivery means is coupled to the proximal end of the transducer transport tube, for maintaining the electrical cable in axial alignment with the transport tube and the fluid delivery means.

The attachment of the electrical cable to the flush valve supports the electrical cable so as to prevent fatigue and kinking of the electrical cable at the point where the cable attaches to the electrical housing. Furthermore, by first attaching the electrical cable to the flush valve, the electrical cable assists in aligning and attaching the flush valve to the blood pressure transducer. Finally, the inventive configuration of axially aligning and attaching the flush valve to the electrical cable simplifies and organizes the layout of the blood pressure monitoring system, making the system more user friendly.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which.

DETAILED DESCRIPTION OF THE PREFERRED EMBODIMENTS

Figure 1:
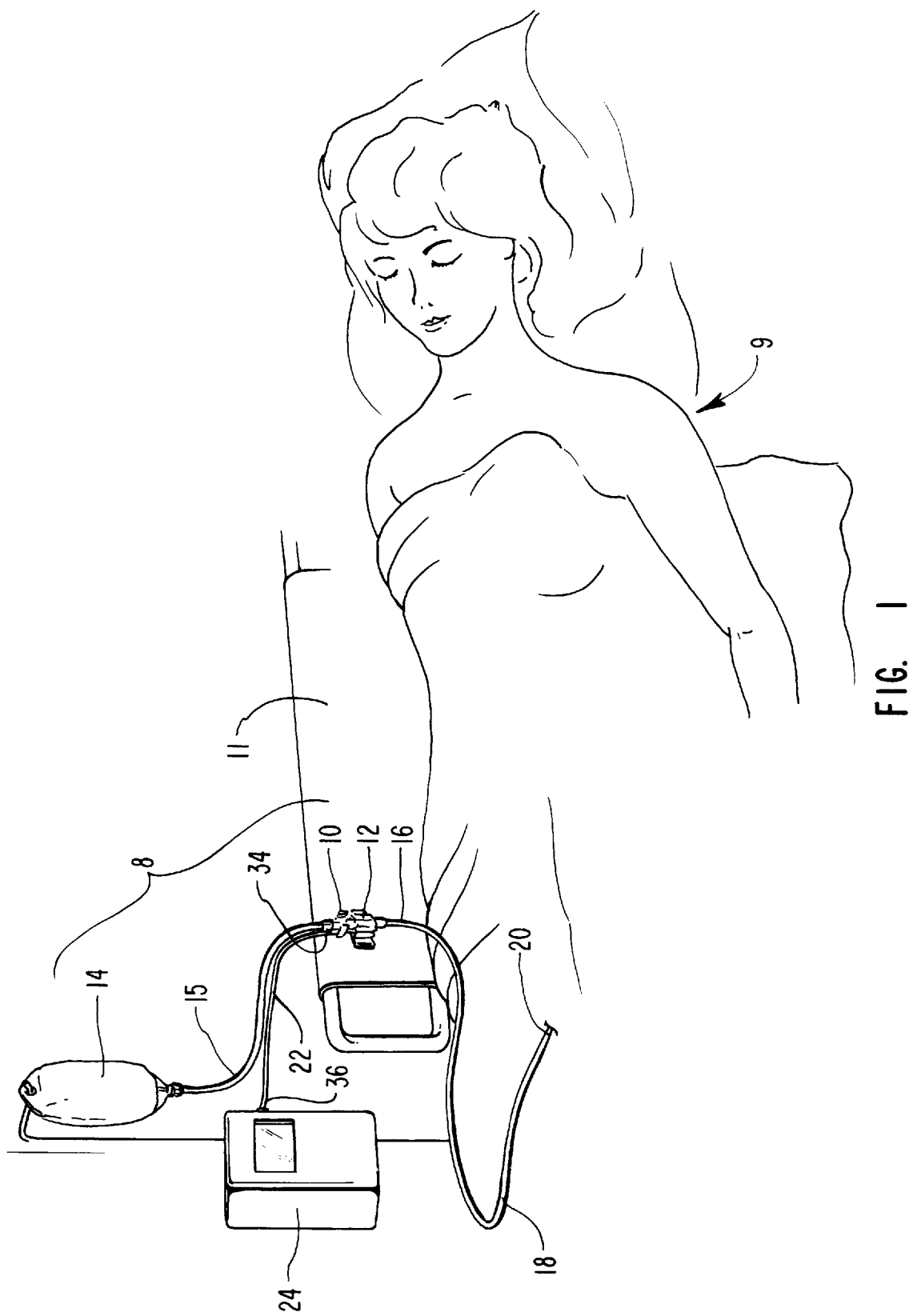
FIG. 1 is a perspective view of a blood pressure monitoring system including a blood pressure transducer with an attached flush valve being coupled by a catheter to the vascular system of a patient.
Figure 2:
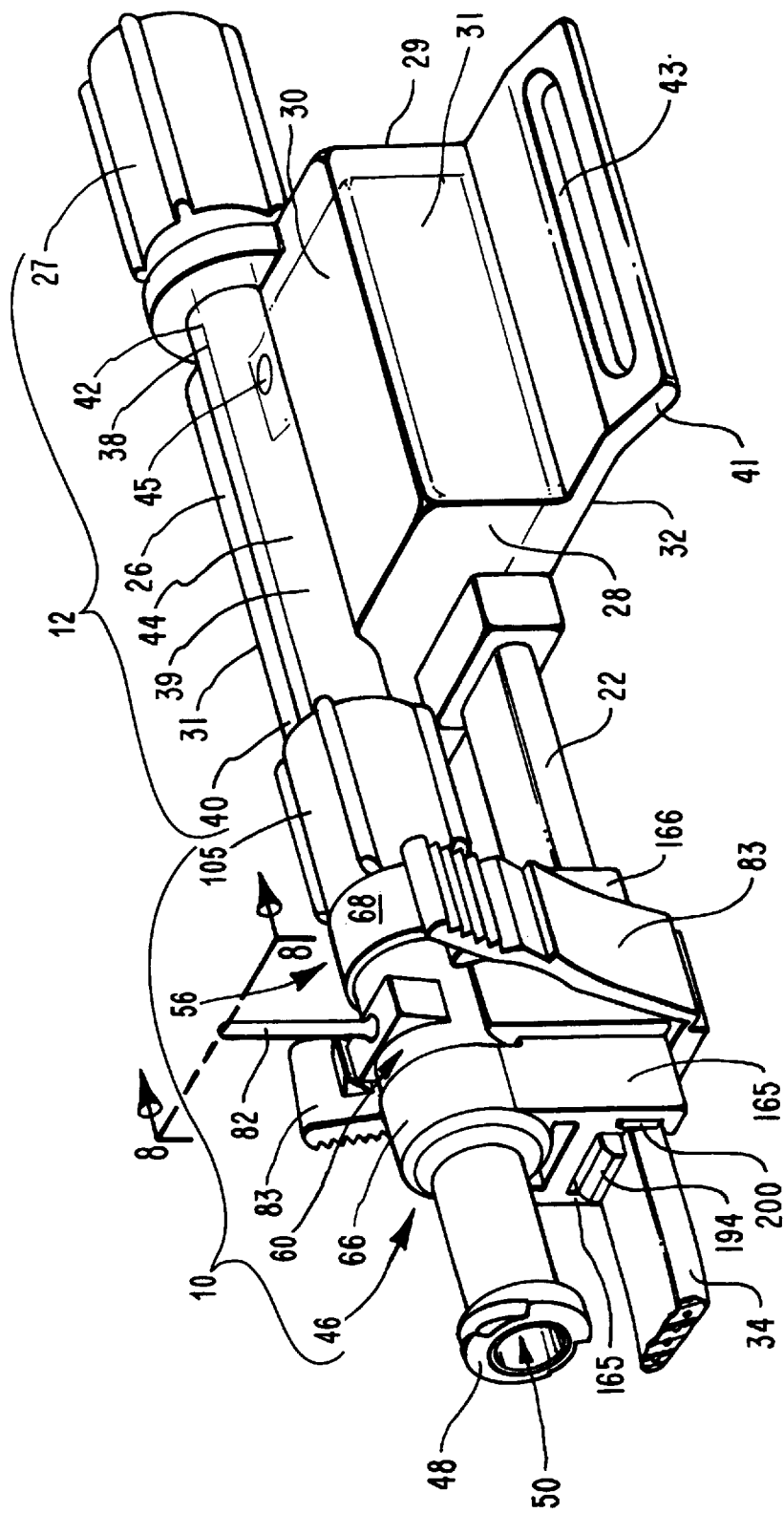
FIG. 2 is an enlarged perspective view of the flush valve and blood pressure transducer shown in FIG. 1.

Depicted in FIGS. 1 and 2 is a system 8 for monitoring the blood pressure and heart rate of a patient 9. System 8 comprises a flush valve 10 fluid coupled at one end to a blood pressure transducer 12. The opposing end of flush valve 10 is fluid coupled to a fluid storage container 14 by a fluid supply tube 15. Transducer 12 is also connected in fluid communication to a proximal end 16 of a catheter 18. Catheter 18 has an opposing distal end 20 that is inserted within patient 9 so as to communicate with the circulatory system of patient 9. System 8 further comprises an electrical cable 22 having a distal end 34 electrically coupled to transducer 12 and an opposing proximal end 36 selectively coupled to a display monitor 24.

During use, fluid in fluid storage container 14, preferably a saline solution containing an anti-blood coagulating agent, flows through fluid supply tube 15 into flush valve 10. The fluid then flows through flush valve 10, transducer 12, and catheter 18 where it eventually merges with the blood in the circulatory system of patient 9. As the heart pumps the blood within patient 9, a compression wave is transferred between the blood and the saline solution within catheter 18. The compression wave travels along catheter 18 to transducer 12 where the wave is converted to an electrical signal. The electrical signal is then transferred along electrical cable 22 to monitor 24. Monitor 24 displays the electrical signal in terms of the patient's heart rate and blood pressure.

Fluid transport tube 38 of transducer 12 is axially aligned with electrical cable 22, a unique and novel embodiment which provides a less cluttered and more convenient arrangement, a significant advantage within the art.

Figure 3:
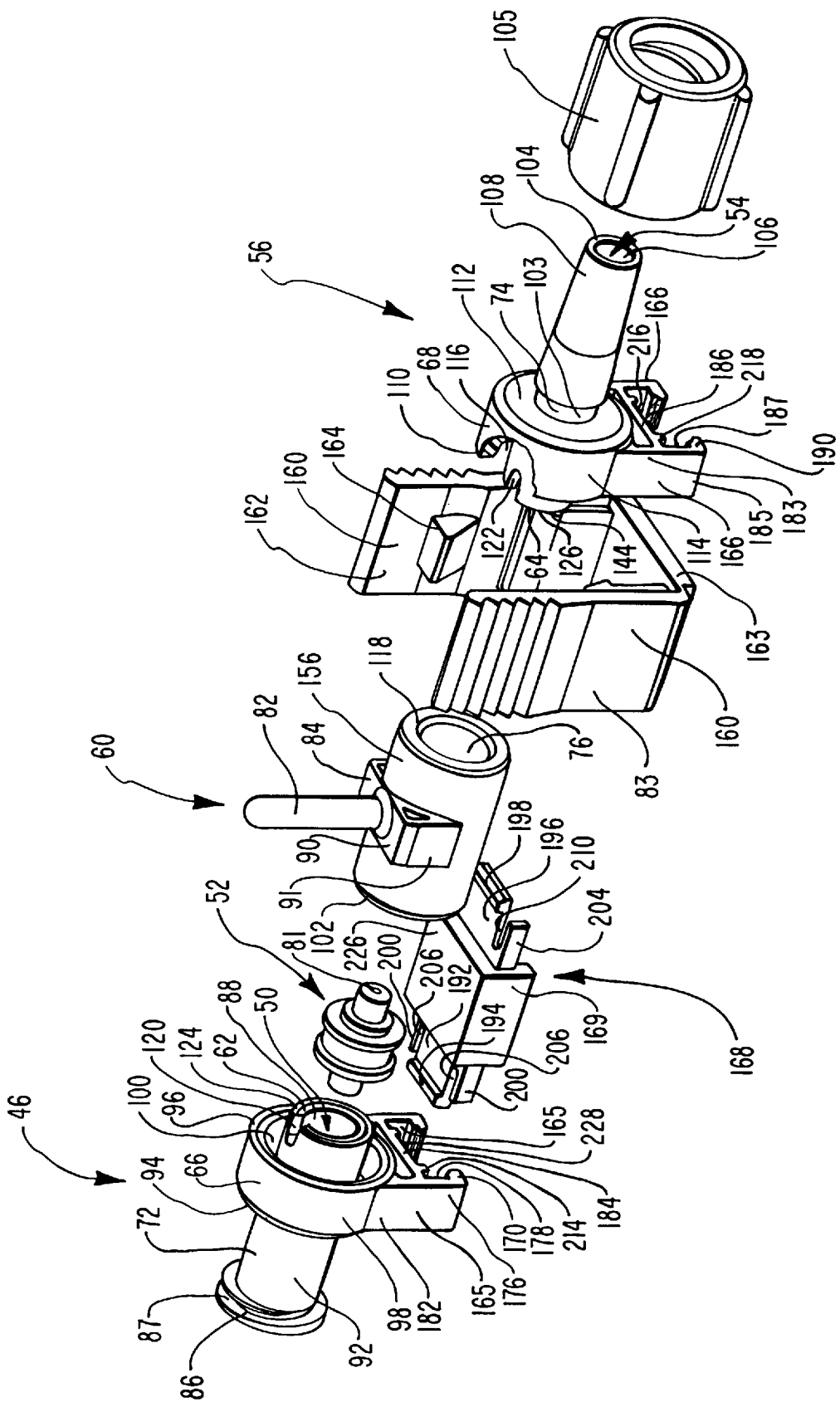
FIG. 3 is an exploded perspective view of the flush valve shown in FIG. 2.
Figure 6:
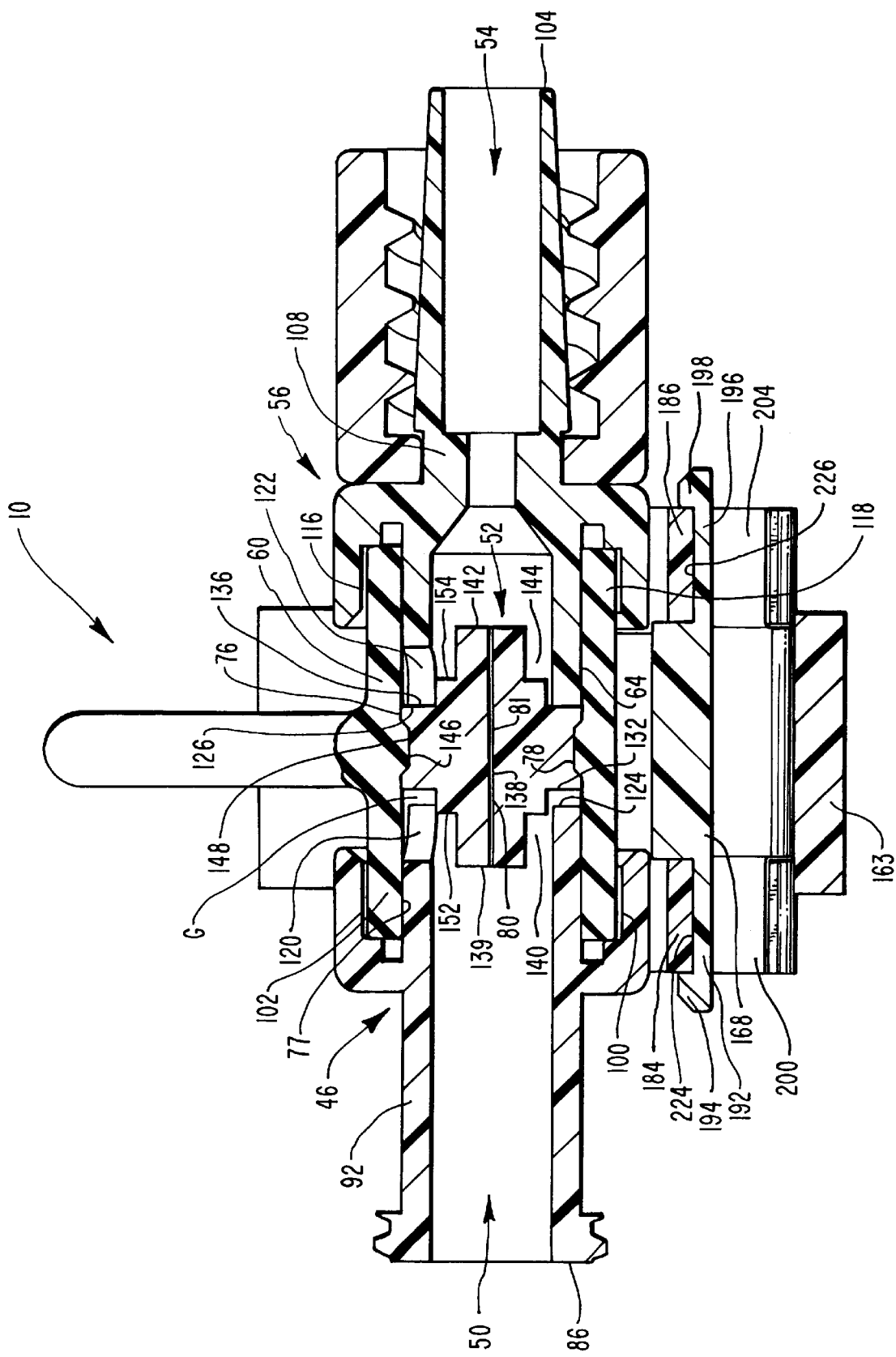
FIG. 6 is a cross-sectional side view of the flush valve shown in FIG. 2 with the sealing tube in a closed position.

With reference now to FIGS. 3 and 6, flush valve 10 is comprised of fluid delivery means for dispensing a fluid at a desired flow rate, the fluid delivery means having a proximal end 86 and a distal end 104. In one embodiment, the fluid delivery means is comprised of (i) an inlet port having a first passageway 50; (ii) an outlet port having a second passageway 54; and (iii) a flow restricting means 52, interposed between and coupled in fluid communication with the inlet port and the outlet port. In one embodiment, the inlet port is comprised of fluid receiving housing 46 while the outlet port is comprised of fluid discharge housing 56, shown in FIGS. 2, 3 and 6. Thus, in this embodiment, the fluid delivery means is comprised of fluid receiving housing 46, fluid discharge housing 56, and member 52 interposed between and coupled in fluid communication with receiving housing 46 and discharge housing 56.

The interior surface of the fluid delivery means includes first passageway 50, second passageway 54, and a capillary tube 80 of flow restricting means 52 disposed therebetween, as shown in FIG. 6. The capillary tube 80 of the fluid delivery means includes a flow restricting passageway defining a primary fluid flow path 81 between the inlet port and the outlet port. Because of the small diameter of the capillary tube 80, fluid flow through the primary fluid flow path 81 is minimized.

Flush valve 10 further includes sealing means for forming a seal about the exterior surface of the flow restricting means 52. Sealing tube 60 is an example of the sealing means. Sealing tube 60 has an interior surface 76 that is disposed about and biased against the exterior surface 78 of the flow restricting means 52. In an alternative embodiment, the sealing means need not include sealing tube 60 but could also comprise a semi-tubular elastomeric member or other comparable structure which could be secured to the exterior surface of the fluid delivery means.

Figure 7:
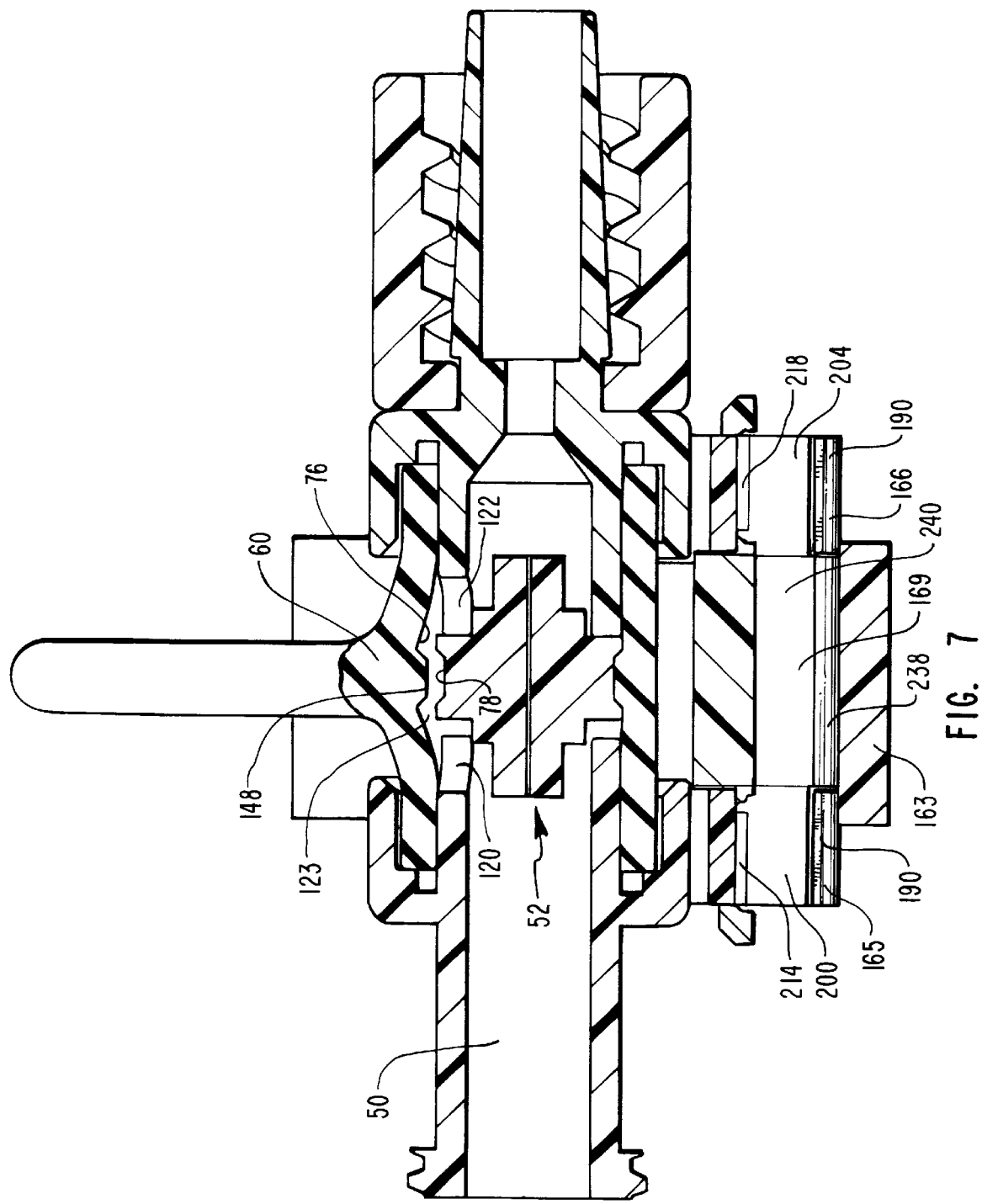
FIG. 7 is a cross-sectional side view of the flush valve shown in FIG. 2 with the sealing tube in an open position.

To increase the amount of flow, flush valve 10 further includes bypass means for selectively forming a secondary fluid flow path 123, shown in FIG. 7, between the inlet port and the outlet port, the secondary fluid flow path 123 being formed between the exterior surface 78 of the flow restricting means 52 and the interior surface 76 of the sealing tube 60 such that the secondary fluid flow path 123 bypasses the primary fluid flow path 81.

To increase the effective seal between the sealing tube 60 and the flow restricting means 52 when the secondary fluid flow path 123 is closed, the exterior surface 78 of the flow restricting means 52 and the interior surface 76 of the sealing means are configured so as to engage one another in an interlocking arrangement so as to increase the effective seal therebetween.

FIG. 2 demonstrates that flush valve 10 is attached to transducer 12 so that distal end 34 of electrical cable 22 is adjacently disposed and longitudinally aligned with flush valve 10. This alignment is accomplished through the use of securing means connected to the fluid delivery means and configured to engage a portion of electrical cable 22 of transducer 12 when the distal end of the fluid delivery means is coupled to the proximal end 40 of transducer transport tube 38, for maintaining electrical cable 22 in axial alignment with transport tube 38 and the fluid delivery means. The securing means mechanically, removably attaches a portion of the electrical cable 22 to the fluid delivery means when the distal end of the fluid delivery means is in fluid communication with proximal end 40 of transport tube 38.

By way of example, one embodiment of the securing means includes first clamping fingers 165, second clamping fingers 166, and third clamping fingers 169, shown in FIGS. 2 and 3. Although the figures of the present invention depict clamping fingers 165, 166, and 169 being used cumulatively, in alternative embodiments of the securing means, it is also envisioned that one or two pairs of the clamping fingers could be used, as will be discussed below.

This configuration of having electrical cable 22 attached and longitudinally aligned with flush valve 10 has several benefits. For example, the present invention allows flush valve 10 to be selectively removed and attached to transducer 12. This allows new or alternative sized flush valves to be used. The prior art transducers have the electrical cable projecting from the electrical housing at a position that is not vertically aligned with the transport tube. Attachment of flush valve 10 and the fluid supply tube 15 thereto requires electrical cable 22 to be biased out of the way for attachment of flush valve 10. In contrast, the configuration of the present invention allows electrical cable 22 to be directly mounted to flush valve 10. This combination assists in the alignment and attachment of flush valve 10 to transducer 12.

Another advantage of attaching electrical cable 22 to flush valve 10 is that electrical cable 22 also becomes aligned with fluid supply tube 15. This configuration provides a more aligned and less cluttered embodiment which is preferred in a patient-care environment. Finally, by attaching electrical cable 22 to flush valve 10, there is a decreased likelihood of fatigue or kinking of electrical cable 22 at the point where electrical cable 22 projects from transducer 12.

The configuration and operation of transducer 12 will now be described in greater detail with continued reference to FIG. 2. As shown therein, transducer 12 preferably comprises an electrical housing 26 having a proximal face 28, a distal face 29, a pair of opposing side faces 31, a top surface 30, and an opposing bottom surface 32. Electrical cable 22 projects from proximal face 28 so as to be aligned with the longitudinal axis of electrical housing 26. Although electrical cable 22 is shown as having a preferred substantially rectangular cross section when viewed from a transverse cross sectional perspective, as will be discussed later, electrical cable 22 can also be configured having alternative cross section shapes such as round, square, or elliptical.

Fluid transport tube 38 is mounted on the top surface 30 of electrical housing 26 above and in axial alignment with electrical cable 22. Transport tube 38 has proximal end 40 projecting past proximal face 28 of electrical housing 26 and a distal end 42 projecting past distal face 29 of electrical housing 26. Formed at proximal end 40 is male luer lock connector (not shown) for selective attachment with flush valve 10. A female luer lock connector 27 is formed at distal end 42 of transport tube 38 for selective attachment to proximal end 16 of catheter 18, as shown in FIG. 1. Thus, in the preferred embodiment, proximal end 40 of transport tube 38 is vertically aligned with distal end 34 of electrical cable 22 when bottom surface 32 of electrical housing 26 is oriented in a horizontal plane.

Transport tube 38 further comprises an interior surface 39 defining a fluid passageway 44 longitudinally extending between proximal end 40 and distal end 42. A flexible diaphragm 45, positioned on top surface 30, communicates with fluid passageway 44 to sense the fluid pressure in transport tube 38. Transducer 12 converts the fluid pressure into electrical signals that are transferred along electrical cable 22 to monitor 24.

Transducer 12 further comprises a pair of wings 41, individually projecting from opposing side faces 31 of electrical housing 26. Each of wings 41 has a slot 43 extending therethrough. Although transducer 12 is shown in FIG. 1 as being mounted on an attachment board 11, slots 43 can be used for securing a strap to transducer 12 so that transducer 12 can be directly attached to a patient's arm or leg.

The configuration and operation of flush valve 10 will now be described in greater detail with continued reference to FIGS. 2–8.

As discussed above, in one embodiment, the inlet port of the fluid delivery means is comprised of fluid receiving housing 46 while the outlet port of the fluid delivery means is comprised of fluid discharge housing 56, shown in FIGS. 2 and 3. In another embodiment, the inlet port is comprised of first tubular body 92 of receiving housing 46 while the outlet port is comprised of second tubular body 108 of discharge housing 56. In an alternative embodiment, the fluid delivery means could include an elongated unitary tube having a constricted portion formed therein, the inlet port and outlet port being on opposing sides of the constricted portion. It is likewise envisioned by the present invention that a variety of different tubular structures could be made having smaller diameter constricting members selectively positioned therein.

To further describe the components and operation of flush valve 10, reference is now made to FIG. 3, which is an exploded view thereof. As shown in FIG. 3, fluid receiving housing 46 includes first tubular body 92 having a distal end 62, an opposing proximal end 86, and an exterior surface 72 extending therebetween. First tubular body 92 further comprises an interior surface 88 defining first fluid passageway 50 longitudinally extending between proximal end 86 and distal end 62.

A male luer lock connector 87 is formed at proximal end 86 of first tubular body 92 for use in attachment to supply tube 15. Distal end 62 of first tubular body 92 terminates in an annular distal end face 124. A first bypass slot 120 is formed between interior surface 88 and exterior surface 72 of first tubular body 92 and extends from distal end face 124 a distance towards proximal end 86 of first tubular body 92.

Fluid receiving housing 46 further includes an annular first collar 66 encircling and extending out from exterior surface 72 of first tubular body 92. First collar 66 has a proximal end face 94, a distal end face 96, and an exterior surface 98 extending therebetween. First collar 66 also has an annular first socket 100 recessed within distal end face 96 between exterior surface 72 of first tubular body 92 and exterior surface 98 of first collar 66 so as to encircle tubular body 92.

As also depicted in FIG. 3, one example of securing means projects from first collar 66. As shown, first pair of flexible clamping fingers 165 project in a parallel configuration from first collar 66. Each of clamping fingers 165 comprise a first end 182 attached to exterior surface 98 of first collar 66, an opposing free second end 176, and an inside face 178 extending therebetween. Extending between inside faces 178 near first end 182 is a support member 184. Support member 184 has a bottom surface 228 with a pair of spaced alignment ridges 214 projecting therefrom. Projecting from inside face 178 of each clamping fingers 165 at second end 176 is a catch lip 170. First pair of clamping fingers 165 and bottom surface 228 of support member 184 define a U-shaped channel.

Turning now to fluid discharge housing 56, fluid discharge housing 56 includes second tubular body 108 having a distal end 104, an opposing proximal end 64, and an exterior surface 74 extending therebetween. Second tubular body 108 further comprises an interior surface 106 defining second fluid passageway 54 longitudinally extending between proximal end 64 and distal end 104. Distal end 104 has a substantially conical configuration with an attachment groove 103 encircling exterior surface 74 thereat. Attachment groove 103 is used for rotatably attaching means for coupling the distal end 104 of the fluid delivery means in fluid communication with the proximal end of the transport tube 38, such as a female luer lock sleeve 105, to body 108. As best shown in FIG. 2, female luer lock sleeve 105 is used in fluid coupling second fluid passageway 54 to fluid passageway 44 of transport tube 38.

Referring again to FIG. 3, proximal end 64 of second tubular body 108 terminates in a proximal end face 126. A second bypass slot 122 is formed between interior surface 106 and exterior surface 74 of second tubular body 108 and extends from proximal end face 126 a distance towards distal end 104 of second tubular body 108.

Discharge housing 56 further includes an annular second collar 68 encircling and extending out from exterior surface 74 of second tubular body 108. Second collar 68 includes a proximal end face 110, a distal end face 112, and an exterior surface 114 extending therebetween. Second collar 68 also has an annular second socket 116 recessed within proximal end face 110 of second collar 68 between exterior surface 74 of second tubular body 108 and exterior surface 114 of second collar 68 so as to encircle second tubular body 108.

As also depicted in FIG. 3, another example of securing means projects from second collar 68. As shown, fluid discharge housing 56 includes second pair of flexible clamping fingers 166 projecting in a parallel configuration. Each of clamping fingers 166 comprise a first end 183 attached to exterior surface 114 of second collar 68, an opposing free second end 185, and an inside face 187 extending therebetween. Extending between inside faces 187 near first end 183 is a support member 186. Support member 186 has a bottom surface 216 with a pair of spaced alignment ridges 218 projecting therefrom. Extending from inside face 187 of each of second clamping fingers 166 at second end 185 is a catch lip 190. Second pair of clamping fingers 166 and bottom surface 216 of support member 186 defines a U-shaped channel.

Sealing tube 60 is also depicted in FIG. 3. As disclosed therein, sealing tube 60 is an elastomeric tube including a proximal end 102, a distal end 118, and an exterior surface 156 extending therebetween. Formed on exterior surface 156 is a platform 84 having a substantially flat top surface 90 and a pair of opposing side walls 9 1. As will be discussed later in greater detail, a tail 82 projects from top surface 90 of platform 84.

Figure 5:
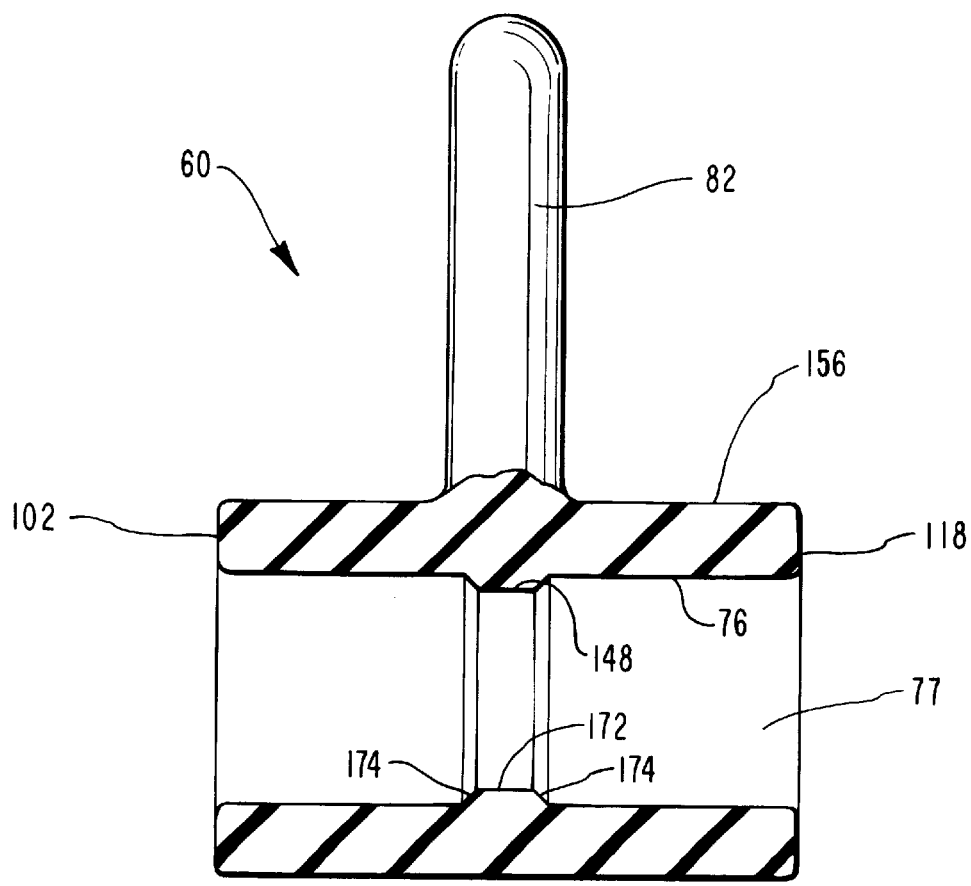
FIG. 5 is an enlarged cross-sectional side view of a sealing tube shown in FIG. 3.

As better depicted in FIG. 5, sealing tube 60 further comprises interior surface 76 defining a lumen 77 longitudinally extending between proximal end 102 and distal end 118. An annular ridge 148 encircles and radially projects inward from interior surface 76. Ridge 148 includes a top surface 172 and a pair of sloping shoulders 174 that extend from top surface 172 to interior surface 76. Sealing tube 60 is formed of a resiliently deformable elastomeric material such as silicon or other medical grade elastomers.

Figure 4:
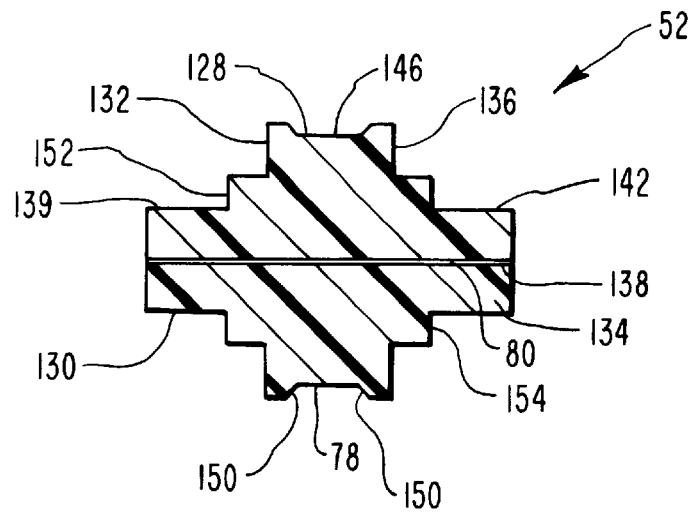
FIG. 4 is an enlarged cross-sectional side view of a flow restricting means shown in FIG. 3.

Referring back to FIG. 3, flush valve 10 is also shown as comprising a flow restricting means 52. As best depicted in FIG. 4, flow restricting means 52 has a proximal end 139, a distal end 142, and an interior surface 138 defining a small diameter capillary tube 80 longitudinally extending therebetween. More specifically, restricting means 52 comprises a cylindrical body 128 having a proximal end face 132, a distal end face 136, and an exterior surface 78 extending therebetween. An annular groove 146 encircles exterior surface 78. Groove 146 has a configuration complementary to the ridge 148 of sealing tube 60.

Flow restricting means 52 further comprises a cylindrical first hub 130 positioned at proximal end 139 and a cylindrical first transition shoulder 152 positioned between first hub 130 and cylindrical body 146. Body 146, first transition shoulder 152, and first hub 130 are axially aligned, with first transition shoulder 152 having an outside diameter greater than the outside diameter of first hub 130 but smaller than the outside diameter of cylindrical body 146.

In like manner, flow restricting means 52 further comprises a cylindrical second hub 134 positioned at distal end 142 and a cylindrical second transition shoulder 154 positioned between second hub 134 and cylindrical body 146. Body 146, second transition shoulder 154, and second hub 134 are axially aligned with second transition shoulder 154 having an outside diameter greater than the outside diameter of second hub 134 but smaller than the outside diameter of cylindrical body 146.

Capillary tube 80 defines a flow restricting passageway defining a primary fluid flow path 81 between the inlet port and the outlet port for dispensing fluid at a desired flow rate. The rate of fluid flow through capillary tube 80 is in part dependent upon the inside diameter of capillary tube 80. By way of example and not be limitation, capillary tube 80 preferably has a diameter of about 0.002 inches when a 2 cubic centimeter per hour flow is desired and a diameter of 0.0034 inches when a 30 cubic centimeter per hour flow is desired.

Assembly of flush valve 10 is accomplished by initially ultrasonically welding distal end face 136 of flow restricting means 52 against proximal end face 126 of second tubular body 108. As depicted in FIG. 6, distal end 142 of flow restricting means 52 is disposed within proximal end 64 of second tubular body 108. Although second transition shoulder 154 is received within second passageway 54, second transition shoulder 154 is configured so as to enable fluid communication between second passageway 54 and second bypass slot 122.

Also shown in FIG. 6, flow restricting means 52, having fluid discharge housing 56 attached thereto, is received within distal end 118 of lumen 77 of sealing tube 60 so that distal end 118 of sealing tube 60 is snugly received within annular second socket 116 of fluid discharge housing 56. The distal interior surface of sealing tube 60 is thus biased against and encircles the proximal exterior surface 74 of second tubular body 108. To position sealing tube 60 within second socket 116, it is preferred to apply a lubricating oil, such as a silicone oil, to the surface of sealing tube 60. Sealing tube 60 is configured to form a liquid tight friction engagement with second socket 116. Flow restricting means 52 is also sufficiently advanced within lumen 77 so that annular ridge 148 on sealing tube 60 is aligned with and received within annular groove 146 on flow restricting means 52.

Finally, distal end 62 of first tubular body 92 is received within proximal end 102 of lumen 77 of sealing tube 60 so that proximal end 102 of sealing tube 60 is snugly received within annular first socket 100 of fluid receiving housing 46. The proximal interior surface of sealing tube 60 is thus biased against and encircles the distal exterior surface 72 of first tubular body 92. Sealing tube 60 is also configured to form a liquid tight friction engagement with first socket 100.

In the embodiment shown in FIG. 6, first tubular body 92 is not directly welded to flow restricting means 52. Accordingly, a gap G typically exists between distal end face 124 of first tubular body 92 and proximal end face 132 of flow restricting means 52. Such a configuration facilitates easy assembly and also permits flexibility of fluid receiving housing 46 relative to fluid discharge housing 56. This flexibility allows for a greater resistance to impact without cracking or failure of flush valve 10. In alternative embodiments, of course, flow restricting means 52 can be independently welded to either or both of first tubular body 92 and second tubular body 108. As will be disclosed later, additional structures are also provided for securing fluid receiving housing 46 to fluid discharge housing 56.

Also as shown in FIGS. 6 and 7, as a result of its elastomeric properties, seal tube 60 can be selectively moved into one of two positions. As depicted in FIG. 6, sealing tube 60 is in an unstressed closed position, covering bypass slots 120, 122. The closed position is denoted by annular ridge 148 being snugly received in a sealed engagement in annular groove 146, thereby precluding fluid communication between first bypass slot 120 and second bypass slot 122, causing fluid to flow within the primary fluid flow path 81. Furthermore, frictional engagement between the opposing ends of sealing tube 60 and the corresponding first socket 100 and second socket 116 precludes fluid from passing between bypass slots 120, 122. As a result, fluid entering proximal end 86 of first passageway 50 is limited to flowing through capillary tube 80 and into second passageway 54.

In the second position of sealing tube 60, the portion of sealing tube 60 adjacent to first bypass slot 120 and second bypass slot 122 is radially outwardly expanded as shown in FIG. 7. As a result, secondary fluid flow path 123 is formed extending from first bypass slot 120 to second bypass slot 122 between interior surface 76 of sealing tube 60 and exterior surface 78 of flow restricting means 52. Secondary fluid flow path 123 can be selectively formed having a much larger cross sectional area than capillary tube 80. As a result, fluid within first passageway 50 is capable of rapidly passing through secondary fluid flow path 123 and into second passageway 54 by bypassing capillary tube 80. Once a desired amount of fluid has passed through secondary fluid flow path 123, sealing tube 60 is allowed to self-constrict resulting in ridge 148 being received within groove 146 so as to bias against the flow restricting means 52 and close off secondary fluid flow path 123.

As referenced above, flush valve 10 further includes bypass means for selectively forming a secondary fluid flow path 123 between the inlet port and the outlet port, the secondary fluid flow path 123 being formed between the exterior surface 78 of the flow restricting means 52 and the interior surface 76 of the sealing means such that the secondary fluid flow path 123 bypasses the primary fluid flow path 81. Secondary fluid flow path 123 thus extends from first passageway 50 to second passageway 54 between exterior surface of the fluid delivery means and the interior surface of sealing tube 60 so that the secondary fluid flow path 123 bypasses capillary tube 80. By way of example and not by limitation, the bypass means includes first bypass slot 120 and second bypass slot 122 as previously discussed with regard to FIGS. 6 and 7, the bypass slots 120, 122 each being selectively covered by the sealing means.

Also as discussed above, the exterior surface of the flow restricting means and the interior surface 76 of the sealing means 60 are configured so as to engage one another in an interlocking arrangement so as to increase the effective seal therebetween when secondary fluid flow path 123 is closed.

By way of example and not by limitation, one embodiment of the interlocking arrangement includes annular ridge 148 of sealing tube 60 and annular groove 146 of flow restricting means 52, as previously discussed above with regard to FIGS. 4–7. The unique and novel interlocking configurations between groove 146 and ridge 148 produce a mating contact that has an improved closed sealed engagement of secondary fluid flow path 123 compared to conventional prior art flush valves. As a result of the interlocking groove and ridge configuration, less annular constricting pressure is required by sealing tube 60 to effectively seal closed secondary fluid flow path 123.

It is believed that certain prior art flush valves have a decreased sealing efficiency because as the secondary fluid flow path 123 is opened, the remaining portion of the sealing tube has an increased friction engagement against the exterior surface of the flow restricting means. When the sealing tube is released to permit self-constricting thereof, the increased friction engagement precludes complete annular constriction of the sealing tube, thereby decreasing the effectiveness of the seal, especially at the point where the secondary fluid flow path 123 is formed.

The inventive ridge 148 and groove 146 configuration is found to decrease the above frictional engagement between sealing tube 60 and exterior surface 78 of flow restricting means 52 when secondary fluid flow path 123 is open. By minimizing the effect of this frictional engagement, the novel ridge and groove configuration of the present invention is better able to repeatedly open and seal closed secondary fluid flow path 123.

The present invention also envisions a plurality of alternative embodiments of the interlocking arrangements. In yet another alternative embodiment, it is envisioned that the complementary groove and ridge configuration need not be positioned directly over the capillary tube but could be positioned either upstream or downstream of the capillary tube. It is necessary only that the complementary ridge and groove configuration be formed between first bypass slot 120 and second bypass slot 122. It is also envisioned that the ridge and complementary groove can have a variety of different configurations including V-shaped, W-shaped, or semi-elliptical. In another embodiment, an annular ridge could be formed encircling and radially extending out from exterior surface 78 of flow restricting means 52 while a complementary groove radially encircles interior surface 76 of sealing tube 60.

Finally, it is also envisioned that the interlocking arrangement could comprise a complementary ridge and groove configuration which only partially encircles sealing tube 60 and flow restricting means 52. That is, ridge 148 may extend only partially around interior surface 76 of sealing tube 60 while groove 146 only extends around a complementary portion of flow restricting means 52. The remaining engaged surface between sealing tube 60 and flow restricting means 52 may comprise abutting smooth faces.

In light of the interlocking arrangement, flush valve 10 produces an increased effective seal to close off the secondary fluid flow path 123. The interlocking arrangement also minimizes leaking of fluid through the secondary fluid flow path after repeated opening and closing of the secondary fluid flow path.

In one embodiment of the present invention, selecting means are provided for selectively positioning sealing tube 60 in the open and closed position. By way of example and not by limitation, the selecting means includes tail 82 projecting from sealing tube 60 as discussed with regard to FIG. 3. By pulling on tail 82, the portion of sealing tube 60 positioned adjacent to first bypass slot 120 and second bypass slot 122 radially expand outward to form secondary fluid flow path 123.

An alternative function of tail 82 is for calibrating blood pressure transducer 12. That is, by pulling and then quickly releasing tail 82, a wave is formed within the saline solution within fluid passageway 44 of transport tube 42. The wave can then be used for calibrating transducer 12.

Figure 8:
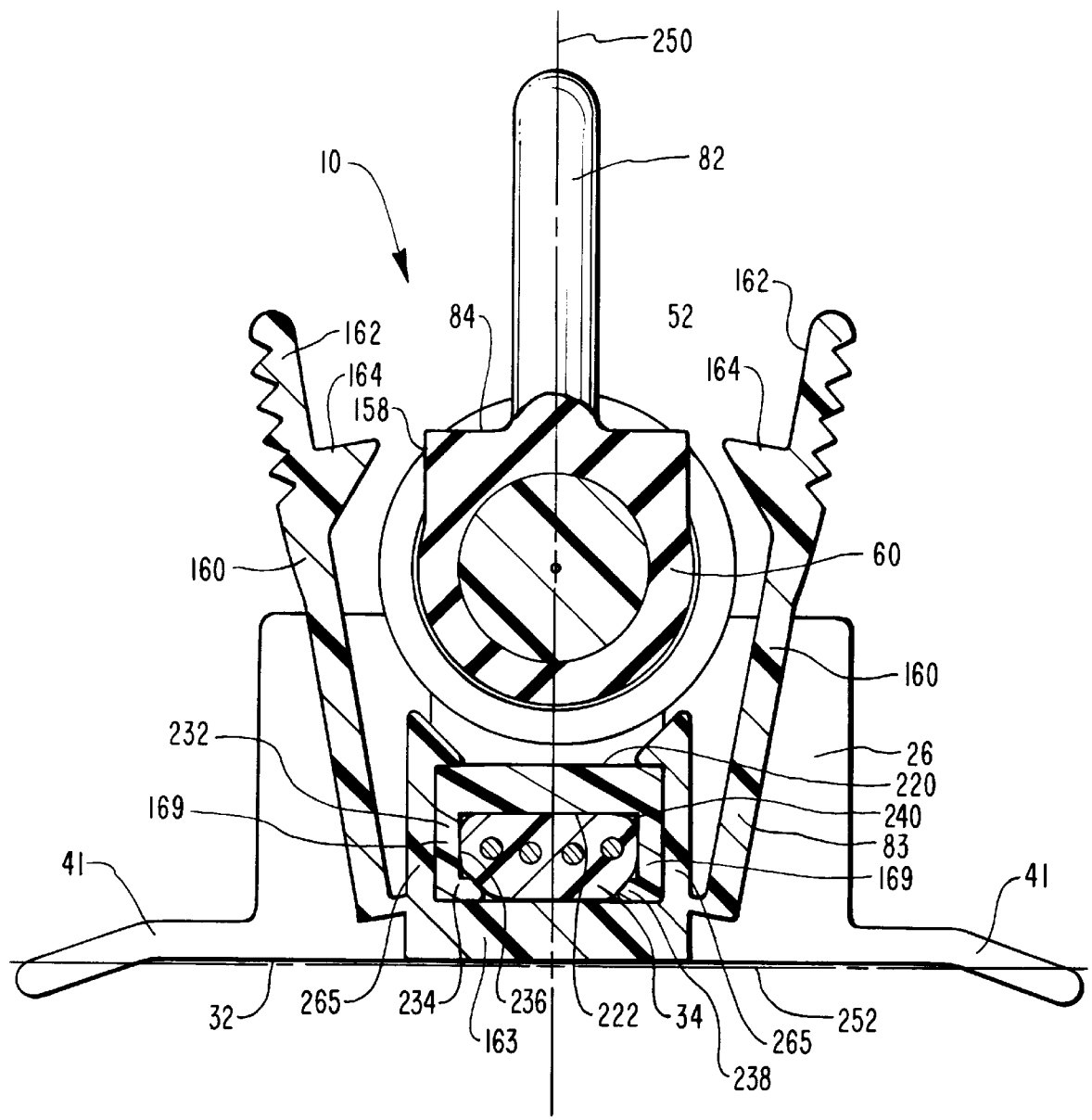
FIG. 8 is a cross sectional end view of the flush valve shown in FIG. 2 taken along section lines 8—8 shown therein.

It An alternative embodiment of the selecting means comprises a clamp 83 as depicted in FIG. 3. Clamp 83 comprises a floor 163 having a pair of flexible arms 160 projecting therefrom. Each of arms 160 have an interior surface 162 with a pinching rib 164 projecting therefrom. As best depicted in FIG. 8, flexible arms 160 are positioned on opposing sides of sealing tube 60 so that pinching ribs 164 are aligned with parallel side walls 158 of platform 84. As arms 160 are compressed radially inward, pinching ribs 164 compress against parallel sidewalls 158 causing the portion of sealing tube 60 above bypass slots 120 and 122 to radially expand outward, thereby forming secondary fluid flow path 123. As also depicted in FIG. 8, clamp 83 is attached to flush valve 10 by a pair of clamping fingers 265 projecting from floor 163 and latching to top surface 220 of body 226.

The present invention further provides attachment means for connecting sealing tube 60 to fluid receiving housing 46 and fluid discharge housing 56 to preclude fluid communication between secondary fluid flow path 123 and the exterior of flush valve 10. By way of example and not by limitation, one embodiment of the attachment means comprises, as previously discussed with regard to FIG. 6, annular first collar 66 including first socket 100 which receives in a sealed frictional engagement proximal end 102 of sealing tube 60. In another embodiment, the attachment means includes second collar 68 including second socket 116 which receives distal end 118 of sealing tube 60 in a sealed friction engagement. Since sealed tube 60 is only frictionally engaged within first socket 100 and second socket 116, in another embodiment, the attachment means includes a connecting plate 168 as depicted in FIG. 3.

Connecting plate 168 comprises a proximal neck 192, a distal neck 196, and a body 226 extending therebetween. As perhaps best depicted in FIG. 8, body 226 comprises a top surface 220 and a bottom surface 222. As an additional example of securing means, projecting from bottom surface 222 in a parallel configuration are a third pair of clamping fingers 169. Each of clamping fingers 169 comprise a first end 232 attached to bottom surface 222 of connecting plate 168, an opposing free second end 234, and an inside face 236 extending therebetween. Projecting from inside face 236 at second end 234 of each of fingers 169 is a catch lip 238. Third pair of clamping fingers 169 and bottom surface 222 define a U-shaped channel.

Referring to FIG. 6, proximal neck 192 has a top surface 224 with a catch lip 194 extending therefrom. In like manner distal neck 196 also includes a top surface 226 with a catch lip 198 projecting therefrom. Referring again to FIG. 3, connecting plate 168 further comprises a flexible first support arm 200 proximally projecting from each of third clamping fingers 169. Each first support arm 200 is configured so that an attachment slot 206 is formed between proximal neck 192 and each first support arm 200. In addition, a flexible second support arm 204 distally projects from each third clamping finger 169. Each second support arm 204 is configured so that an attachment slot 210 is formed between distal neck 196 and each second support arm 204.

With continued reference to FIG. 3, during assembly, proximal neck 192 of connecting plate 168 is received between alignment ridges 214 on fluid receiving housing 46 so that each support arm 200 is laterally biased against inside faces 178 of first clamping fingers 165. Connecting plate is advanced until catch lip 194 latches against the proximal side of support member 184, as depicted in FIG. 6, thereby forming a mechanical connection between connecting plate 168 and fluid receiving housing 46. In this position, connecting plate 168 and fluid receiving housing 46 are also preferably glued or ultrasonically welded together.

In like manner, distal neck 196 of connecting plate 168 is received between alignment ridges 218 on fluid discharge housing 56 so that each support arm 204 is laterally biased against inside faces 187 of second clamping fingers 166. Connecting plate 168 is advanced until catch lip 198 latches against the distal side of support member 186, as depicted in FIG. 6, thereby forming a mechanical connection between connecting plate 168 and fluid discharge housing 56. In this position, connecting plate 168 and fluid discharge housing 56 are also preferably glued or ultrasonically welded together.

The attachment of connecting plate 168 to the fluid discharge housing 56 and fluid receiving housing 46 holds fluid discharge housing 56 and fluid receiving housing 46 relatively stationary with respect to each other. As such, proximal end 102 of sealing tube 60 is precluded from being retracted from first socket 100 and distal end 118 of sealing tube 60 is precluded from being retracted from second socket 116. Retraction of sealing tube 60 from sockets 100 and 116 would result in fluid leakage therebetween.

The present invention also envisions a plurality of alternative attachment means, by way of example, it is envisioned that rather than using connecting plate 168, sealing tube 60 could be glued or welded within sockets 100 and 116. Alternatively, it is envisioned that a frictional engagement could be obtained between sealing tube 60 and sockets 100 and 116, such as by press fitting seal tube 60 within sockets 100 and 116, which would preclude the opposing ends of sealing tube 60 from retracting out of sockets 110 and 116. In yet another embodiment, annular collars 66 and 68 and connecting plate 168 could be eliminated by directly gluing or welding the opposing ends of sealing tube 60 directly to the exterior surfaces of first tubular body 92 and second tubular body 108. Likewise, alternative clamping or tying structures could be used for securing opposing ends of sealing tube 60 against the exterior surfaces of first tubular body 92 and second tubular body 108.

First, second, and third pairs of clamping fingers have been discussed as examples of securing means, collectively and individually. The above discussed attachment of connecting plate 168 to fluid discharge housing 56 and fluid receiving housing 46 also results in first pair of clamping fingers 165, second pair of clamping fingers 166, and third pair of clamping fingers 169 being longitudinally aligned so that a U-shaped channel 240 for receiving and retaining cable 22 is formed therethrough, as shown in FIGS. 7 and 8. U-shaped channel 240 is thus another embodiment of a securing means.

As shown in FIG. 8, both flush valve 10 and proximal end 40 of transport tube 38 are vertically aligned with distal end 34 of electrical cable 22 when bottom surface 32 of the electrical housing 26 is horizontally disposed, resulting in an advantageous alignment and connection between flush valve 10 and electrical cable 22, as discussed above. This alignment prevents kinking and drooping of electrical cable 22 as it exists transducer 12. Another advantage of attaching electrical cable 22 to flush valve 10 is that electrical cable 22 also becomes aligned with fluid supply tube 15. This configuration provides a less cluttered embodiment, which is preferred in a patient-care environment.

Also as shown in FIG. 8, U-shaped channel 240 is thus aligned with electrical cable 22 when distal end 104 of fluid discharge housing 56 is fluid coupled to proximal end 40 of transport tube 38. Each of the clamping fingers in pairs 165, 166, and 169 are spaced so that electrical cable 22 can be removably received and retained between the fingers and, in a preferred embodiment, within U-shaped channel 240. Once electrical cable 22 is received within U-shaped channel 240, clamp 83 can be attached to flush valve 10 as previously discussed and depicted in FIG. 8. As a result, floor 163 of clamp 83 encloses a portion of electrical cable 22 and assists in maintaining cable 22 within U-shaped channel 240.

In yet another embodiment of securing means, the clamping fingers need not be attached directly to first collar 66 and second collar 68 but could be attached anywhere on the exterior surface of fluid receiving housing 46 and fluid discharge housing 56. In yet other alternative embodiments of the securing means, a variety of different clamping configurations could be used. For example, an L-shaped clamp could be used for sliding electrical cable 22 into the clamp from the side rather than from directly below flush valve 10. In yet other alternative embodiments, the clamping fingers would be configured to receive electrical cables having a variety of alternative cross-sectional shapes as previously discussed.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A flush valve, comprising:
   an inlet port;
   an outlet port;
   flow restricting means, interposed between and coupled in fluid communication with the inlet port and the outlet port, the flow restricting means having an exterior surface and a passageway, the passageway defining a primary fluid flow path between the inlet port and the outlet port for dispensing a fluid at a desired flow rate;
   sealing means for forming a seal about the exterior surface of the flow restricting means, the sealing means having an interior surface that is disposed about and biased against the exterior surface of the flow restricting means;
   bypass means for selectively forming a secondary fluid flow path between the inlet port and the outlet port, the secondary fluid flow path being formed between the exterior surface of the flow restricting means and the interior of the sealing means such that the secondary fluid flow path bypasses the primary fluid flow path; and means for engaging the exterior surface of the flow restricting means and the interior surface of the sealing means in a mated, interlocking arrangement so as to increase the effective seal therebetween when the secondary fluid flow path is closed.

2. A flush valve as recited in claim 1, wherein the sealing means comprises an elastomeric sealing tube and wherein the interior surface of the sealing tube encircles and is biased against the exterior surface of the flow restricting means.

3. A flush valve as recited in claim 1, wherein the bypass means comprises:
(a) a first bypass slot extending from an interior surface of the inlet port to an exterior surface of the inlet port; and
(b) a second bypass slot extending from an interior surface of the outlet port to an exterior surface of the outlet port, the first bypass slot and the second bypass slot each being selectively covered by the sealing means.

4. A flush valve as recited in claim 1, wherein said means for engaging comprises a groove formed on the exterior surface of the fluid restricting means and a ridge that projects from the interior surface of the sealing means, the ridge being configured so as to be complementary with and received within the groove on the fluid restricting means.

5. A flush valve as recited in claim 4, wherein the groove encircles the exterior surface of the fluid restricting means and the ridge encircles the interior surface of the sealing means.

6. A flush valve as recited in claim 1, wherein:
the inlet port comprises a first tubular body having a distal end, a proximal end, and an exterior surface extending therebetween, the first tubular body further comprising an interior surface defining the first passageway longitudinally extending between the proximal end of the first tubular body and the distal end of the first tubular body; and
the outlet port comprises a second tubular body having a distal end, a proximal end, and an exterior surface extending therebetween, the second tubular body further comprising an interior surface defining the second passageway longitudinally extending between the proximal end of the second tubular body and the distal end of the second tubular body.

7. A flush valve for delivering a fluid to a blood pressure transducer, the flush valve comprising:
(a) a fluid delivery means for dispensing fluid at a desired flow rate, the fluid delivery means having an exterior surface and an interior surface, the interior surface including a first passageway, a second passageway, and a capillary tube disposed in fluid communication between the first passageway and the second passageway;
(b) a sealing tube having an interior surface encircling and biased against the exterior surface of the fluid delivery means, the sealing tube being made of a resiliently deformable, elastomeric material to enable the sealing tube to be radially expanded away from the exterior surface of the fluid delivery means;
(c) bypass means for selectively forming a secondary fluid flow path from the first passageway to the second passageway between the exterior surface of the fluid delivery means and the interior surface of the sealing tube so that the secondary fluid flow path bypasses the capillary tube; and means for engaging the exterior surface of the flow restricting means and the interior surface of the sealing means in a mated, interlocking arrangement so as to increase the effective seal therebetween when the secondary fluid flow path is closed.

8. A flush valve as recited in claim 7, wherein the bypass means comprises:
(a) a first bypass slot extending from the first passageway to the exterior surface of the fluid delivery means; and
(b) a second bypass slot extending from the second passageway to the exterior surface of the fluid delivery means, the first bypass slot and the second bypass slot each being selectively covered by the sealing tube.

9. A flush valve as recited in claim 8, wherein said means for engaging comprises a groove formed on the exterior surface of the fluid restricting means and a ridge that projects from the interior surface of the sealing means, the ridge being configured so as to be complementary with and received within the groove on the fluid restricting means.

10. A flush valve as recited in claim 9, wherein the groove encircles the exterior surface of the fluid delivery means and the ridge encircles the interior surface of the sealing tube.

11. A flush valve as recited in claim 7, further comprising a tail radially projecting out from the exterior surface of the sealing tube, the tail being positioned so that as the tail is pulled, a portion of the sealing tube radially expands outward.

12. A flush valve as recited in claim 7, further comprising a pair of clamping fingers projecting from the exterior surface of the fluid delivery means.

13. A flush valve as recited in claim 7, wherein the fluid delivery means comprises:
(a) a first tubular body having a distal end, a proximal end, and an exterior surface extending therebetween, the first tubular body further comprising an interior surface defining the first passageway longitudinally extending between the proximal end of the first tubular body and the distal end of the first tubular body;
(b) a second tubular body having a distal end, a proximal end, and an exterior surface extending therebetween, the second tubular body further comprising an interior surface defining the second passageway longitudinally extending between the proximal end of the second tubular body and the distal end of the second tubular body; and
(c) a flow restricting means having a proximal end, a distal end, and an exterior surface extending therebetween, the flow restricting means also having an interior surface defining the capillary tube longitudinally extending between the proximal end and the distal end of the flow restricting means, the proximal end of the capillary tube being in fluid communication with the first passageway of the first tubular body, and the distal end of the capillary tube being in fluid communication with the second passageway of the second tubular body.

14. A flush valve comprising:
(a) a fluid receiving housing comprising:
(i) a first tubular body having a distal end, a proximal end, and an exterior surface extending therebetween, the first tubular body further comprising an interior surface defining a first passageway longitudinally extending between the proximal end of the first tubular body and the distal end of the first tubular body; and (ii) a first bypass slot formed at the distal end of the first tubular body and extending between the interior surface of the first tubular body and the exterior surface of the first tubular body;

(b) a fluid discharge housing comprising:

(i) a second tubular body having a distal end, a proximal end, and an exterior surface extending therebetween, the second tubular body further comprising an interior surface defining a second passageway longitudinally extending between the proximal end of the second tubular body and the distal end of the second tubular body; and (ii) a second bypass slot formed at the proximal end of the second tubular body and extending between the interior surface of the second tubular body and the exterior surface of the second tubular body;

(c) a flow restricting means having a proximal end, a distal end, and an exterior surface extending therebetween, the flow restricting means also having an interior surface defining a capillary tube longitudinally extending between the proximal end and the distal end of the flow restricting means, the proximal end of the capillary tube being in fluid communication with the first passageway of the fluid receiving housing, and the distal end of the capillary tube being in fluid communication with the second passageway of the fluid discharge housing;

(d) a sealing tube having a proximal end, a distal end, and an interior surface defining a lumen longitudinally extending therebetween, the lumen housing the distal end of the first tubular body including the first bypass slot, the flow restricting means, and the proximal end of the second tubular body including the second bypass slot, the sealing tube being made of a resiliently deformable, elastomeric material to enable the sealing tube to be selectively operable in one of two positions:

(i) a closed position in which the interior surface of the sealing tube is biased against the exterior surface of the restricting means to preclude fluid communication from the first bypass slot to the second bypass slot between the interior surface of the sealing tube and the exterior surface of the flow restricting means; and (ii) an open position in which the interior surface of the sealing tube is radially expanded to form a secondary fluid flow path extending from the first bypass slot to the second bypass slot between the interior surface of the sealing tube and the exterior surface of the restricting means;

(e) attachment means for connecting the sealing tube to the fluid receiving housing and the fluid discharge housing to preclude fluid communication between the secondary fluid flow path and the exterior of the flush valve, wherein the exterior surface of the flow restricting means and the interior surface of the sealing tube are configured so as to engage one another in an interlocking arrangement so as to increase the effective seal therebetween when the secondary fluid flow path is closed.

15. A flush valve as recited in claim 14, wherein an annular groove encircles the flow restricting means on the exterior surface of the flow restricting means, and an annular ridge encircles and radially projects from the interior surface of the sealing tube, the ridge being configured to be received within the annular groove on the flow restricting means.

16. A flush valve as recited in claim 15, wherein the flow restricting means comprises:

(a) a cylindrical body having a proximal end face, a distal end face, and an exterior surface extending therebetween, the annular groove being formed on the exterior surface of the cylindrical body;

(b) a proximal hub extending from the proximal end face of the cylindrical body, the proximal hub being received within the first passageway in the receiving housing; and (c) a distal hub extending from the distal end face of the cylindrical body, the distal hub being received within the second passageway in the discharge housing, the capillary tube longitudinally extending through the proximal hub, the cylindrical body, and the distal hub.

17. A flush valve as recited in claim 14, wherein the attachment means comprises an annular first collar encircling and extending out from the exterior surface of the first tubular body, the first collar having a proximal end face, a distal end face, and an exterior surface extending therebetween, the first collar also having an annular socket recessed within the distal end face of the first collar so as to encircle the first tubular body, the proximal end of the sealing tube being received within the socket on the first collar.

18. A flush valve as recited in claim 14, wherein the attachment means comprises an annular second collar encircling and extending out from the exterior surface of the second tubular body, the second collar having a proximal end face, a distal end face, and an exterior surface extending therebetween, the second collar also having an annular socket recessed within the proximal end face so as to encircle the second tubular body, the distal end of the sealing tube being received within the socket on the second collar.

19. A flush valve as recited in claim 17, further comprising a pair of clamping fingers projecting from the exterior surface of the first collar on the first tubular body.

20. A flush valve as recited in claim 14, wherein the attachment means further comprises a connecting plate rigidly connecting the exterior surface of the receiving housing to the exterior surface of the discharge housing.

21. A flush valve as recited in claim 18, further comprising a pair of clamping fingers projecting from the exterior surface of the second collar on the second tubular body.

22. A flush valve as recited in claim 14, further comprises selecting means for selectively positioning the sealing tube in the open and closed position.

23. A flush valve as recited in claim 19, wherein the selecting means comprises a tail radially projecting out from the exterior surface of the sealing tube, the tail being positioned so that as the tail is pulled, a portion of the sealing tube radially expands to position the sealing tube into the open position.

24. A flush valve as recited in claim 19, wherein the selecting means comprises:

(a) a platform having a pair of parallel side walls formed on the exterior surface of the sealing tube; and (b) a clamp having a pair of flexible arms positioned on opposing sides of the sealing tube, each of the arms having an interior surface with a pinching rib projecting therefrom, the pinching ribs being positioned so that as the flexible arms are pressed together, the pinching ribs bias against the parallel side walls causing a portion of the sealing tube to radially expand into the open position.

25. A flush valve as recited in claim 14, wherein the first tubular body has a distal end face and the first bypass slot is formed at the distal end face of the first tubular body and extends a distance towards the proximal end of the first tubular body.

26. A flush valve comprising:
(a) a fluid receiving housing comprising:
  (i) a first tubular body having a distal end, a proximal end, and an exterior surface extending therebetween, the first tubular body further comprising an interior surface defining a first passageway longitudinally extending between the proximal end of the first tubular body and the distal end of the first tubular body; and
  (ii) a first bypass slot formed at the distal end of the first tubular body and extending between the interior surface of the first tubular body and the exterior surface of the first tubular body;
(b) a fluid discharge housing comprising:
  (i) a second tubular body having a distal end, a proximal end, and an exterior surface extending therebetween, the second tubular body further comprising an interior surface defining a second passageway longitudinally extending between the proximal end of the second tubular body and the distal end of the second tubular body; and
  (ii) a second bypass slot formed at the proximal end of the second tubular body and extending between the interior surface of the second tubular body and the exterior surface of the second tubular body;
(c) a flow restricting means having a proximal end, a distal end, and an exterior surface extending therebetween, the flow restricting means also having:
  (i) an interior surface defining a capillary tube longitudinally extending between the proximal end and the distal end of the flow restricting means, the proximal end of the capillary tube being in fluid communication with the first passageway of the fluid receiving housing, and the distal end of the capillary tube being in fluid communication with the second passageway of the fluid discharge housing; and
  (ii) an annular groove encircling the flow restricting means on the exterior surface;
(d) a sealing tube having a proximal end, a distal end, and an exterior surface extending therebetween, the sealing tube further comprising:
  (i) an interior surface defining a lumen longitudinally extending between the proximal end and the distal end of the sealing tube, the lumen housing the distal end of the first tubular body including the first bypass slot, the flow restricting means, and the proximal end of the second tubular body including the second bypass slot; and
  (ii) an annular ridge encircling and radially projecting from the interior surface of the sealing tube, the ridge being configured to be received within the annular groove on the restricting means, the sealing tube being made of a resiliently deformable, elastomeric material to enable the sealing tube to be selectively operable in one of two positions:
    (A) a closed position in which the annular ridge on the interior surface of the sealing tube is received within the groove on the exterior surface of the restricting means to preclude fluid communication from the first bypass slot to the second bypass slot between the interior surface of the sealing tube and the exterior surface of the restricting means; and
    (B) an open position in which the interior surface of the sealing tube is radially expanded to form a fluid flow path extending from the first bypass slot to the second bypass slot between the interior surface of the sealing tube and the exterior surface of the restricting means; and
(e) attachment means for connecting the sealing tube to the fluid receiving housing and the fluid discharge housing to preclude fluid communication between the secondary fluid flow path and the exterior of the flush valve.

27. A flush valve as recited in claim 26, wherein the attachment means comprises an annular first collar encircling and extending out from the exterior surface of the first tubular body, the first collar having a proximal end face, a distal end face, and an exterior surface extending therebetween, the first collar also having an annular socket recessed within the distal end face of the first collar so as to encircle the first tubular body, the proximal end of the sealing tube being received within the socket on the first collar.

28. A flush valve as recited in claim 26, wherein the attachment means comprises an annular second collar encircling and extending out from the exterior surface of the second tubular body, the second collar having a proximal end face, a distal end face, and an exterior surface extending therebetween, the second collar also having an annular socket recessed within the proximal end face so as to encircle the second tubular body, the distal end of the sealing tube being received within the socket on the second collar.

29. A flush valve as recited in claim 26, wherein the attachment means comprises a connecting plate rigidly connecting the exterior surface of the receiving housing to the exterior surface of the discharge housing.

30. A flush valve as recited in claim 29, further comprising a pair of clamping fingers projecting from the connecting plate.

31. A flush valve as recited in claim 26, wherein the sealing tube further comprises a tail radially projecting out from the exterior surface of the sealing tube, the tail being positioned so that as the tail is pulled, a portion of the sealing tube radially expands to position the sealing tube into the open position.

32. A flush valve as recited in claim 26, wherein the flush valve further comprises:
(a) a platform having a pair of parallel side walls formed on the exterior surface of the sealing tube; and
(b) a clamp having a pair of flexible arms positioned on opposing sides of the sealing tube, each of the arms having an interior surface with a pinching rib projecting therefrom, the pinching ribs being positioned so that as the flexible arms are pressed together, the pinching ribs bias against the parallel side walls causing a portion of the sealing tube to radially expand into the open position.

33. A flush valve as recited in claim 26, wherein the flow restricting means comprises:
(a) a cylindrical body having a proximal end face, a distal end face, and an exterior surface extending therebetween, the annular groove being formed on the exterior surface of the cylindrical body;
(b) a proximal hub extending from the proximal end face of the cylindrical body, the proximal hub being received within the first passageway in the receiving housing; and
(c) a distal hub extending from the distal end face of the cylindrical body, the distal hub being received within the second passageway in the discharge housing, the capillary tube longitudinally extending through the proximal hub, the cylindrical body, and the distal hub.

34. A flush valve as recited in claim 26, wherein the second tubular body has a proximal end face and the second bypass slot is formed at the proximal end face of the second tubular body and extends a distance towards the distal end of the second tubular body.

35. A system for monitoring blood pressure, the system comprising:
(a) a blood pressure transducer comprising:
  (i) an electrical housing;
  (ii) an electrical cable having a distal end attached to the electrical housing and an opposing free proximal end; and
  (iii) a fluid transport tube mounted on the electrical housing above and in axial alignment with the electrical cable, the transport tube having a proximal end, a distal end, and a fluid passageway longitudinally extending therebetween; and
(b) a flush valve coupled in fluid communication with the proximal end of the transport tube, comprising:
an inlet port;
an outlet port;
flow restricting means, interposed between and coupled in fluid communication with the inlet port and the outlet port, the flow restricting means having an exterior surface and a passageway, the passageway defining a primary fluid flow path between the inlet port and the outlet port for dispensing a fluid at a desired flow rate;
sealing means for forming a seal about the exterior surface of the flow restricting means, the sealing means having an interior surface that is disposed about and biased against the exterior surface of the flow restricting means;
bypass means for selectively forming a secondary fluid flow path between the inlet port and the outlet port, the secondary fluid flow path being formed between the exterior surface of the flow restricting means and the interior of the sealing means such that the secondary fluid flow path bypasses primary fluid flow path; and
means for engaging the exterior surface of the flow restricting means and the interior surface of the sealing means in a mated, interlocking arrangement so as to increase the effective seal therebetween when the secondary fluid flow path is closed.

36. A system as recited in claim 35, wherein the bypass means comprises:
(a) a first bypass slot extending from the first passageway to the exterior surface of the flow restricting member; and
(b) a second bypass slot extending from the second passageway to the exterior surface of the flow restricting member, the first bypass slot and the second bypass slot each being selectively covered by the sealing tube.

37. A flush valve as recited in claim 35, wherein said means for engaging comprises a groove formed on the exterior surface of the fluid restricting means and a ridge that projects from the interior surface of the sealing means, the ridge being configured so as to be complementary with and received within the groove on the fluid restricting means.

38. A system as recited in claim 35, further comprising a tail radially projecting out from the exterior surface of the sealing tube, the tail being positioned so that as the tail is pulled, a portion of the sealing tube radially expands outward.

39. A system as recited in claim 35, wherein:
the inlet port comprises a first tubular body having a distal end, a proximal end, and an exterior surface extending therebetween, the first tubular body further comprising an interior surface defining the first passageway longitudinally extending between the proximal end of the first tubular body and the distal end of the first tubular body; and
the outlet port comprises a second tubular body having a distal end, a proximal end, and an exterior surface extending therebetween, the second tubular body further comprising an interior surface defining the second passageway longitudinally extending between the proximal end of the second tubular body and the distal end of the second tubular body.

40. A system as recited in claim 35, wherein the flush valve further comprises:
(a) a platform having a pair of parallel side walls formed on the exterior surface of the sealing tube; and
(b) a clamp having a pair of flexible arms positioned on opposing sides of the sealing tube, each of the arms having an interior surface with a pinching rib projecting therefrom, the pinching ribs being positioned so that as the flexible arms are pressed together, the pinching ribs bias against the parallel side walls causing a portion of the sealing tube to radially expand into the open position.

41. A system as recited in claim 35, further comprising securing means, connected to the flow restricting member and configured to engage a portion of the electrical cable for maintaining the electrical cable in axial alignment with the transport tube and the flow restricting member.

42. A system as recited in claim 41, wherein the securing means comprises a pair of clamping fingers projecting from the exterior surface of the flow restricting member, the clamping fingers being configured to receive and retain a portion of the electrical cable.

43. A system as recited in claim 35, wherein the distal end of the electrical cable and the proximal end of the transport tube are vertically aligned when the electrical housing is horizontally disposed.

44. A system as recited in claim 35, wherein the distal end of the electrical cable and the flush valve are vertically aligned when the electrical housing is horizontally disposed.

* * * * *

UNITED STATES PATENT AND TRADEMARK OFFICE
CERTIFICATE OF CORRECTION

PATENT NO. : 5,820,565
DATED : October 13, 1998
INVENTOR(S) : Gregory R. Mcarthur It is certified that error appears in the above-identified patent and that said Letters Patent is hereby corrected as shown below:

Col. 9, ln. 36: after "and not" change "be" to --by--

Col. 12, ln. 19: before "An alternative" delete [It]

Col. 18, ln 31: after "claim" change "17" to --18--

Col.18, ln 38: after "claim" change "18" to --20--

Col. 18, ln 45: after "claim" change "19" to --22--

Col. 18, ln 51: after "claim" change "19" to --22--

Signed and Sealed this

Thirtieth Day of May, 2000

Attest:

Q. TODD DICKINSON

Attesting Officer     Director of Patents and Trademarks